US011510662B2

(12) United States Patent
Baril et al.

(10) Patent No.: US 11,510,662 B2
(45) Date of Patent: Nov. 29, 2022

(54) FREE STANDING BAG WITH INTEGRATED CUTTING GUARD INTERFACE

(71) Applicant: COVIDIEN LP, Mansfield, MA (US)

(72) Inventors: Jacob C. Baril, Norwalk, CT (US); Saumya Banerjee, Hamden, CT (US); Matthew A. Dinino, Newington, CT (US); Justin J. Thomas, New Haven, CT (US); Roy J. Pilletere, North Haven, CT (US)

(73) Assignee: COVIDIEN LP, Mansfield, MA (US)

( * ) Notice: Subject to any disclaimer, the term of this patent is extended or adjusted under 35 U.S.C. 154(b) by 680 days.

(21) Appl. No.: 16/520,480

(22) Filed: Jul. 24, 2019

(65) Prior Publication Data

US 2021/0022719 A1 Jan. 28, 2021

(51) Int. Cl.
*A61B 17/00* (2006.01)
*A61B 18/16* (2006.01)
*A61B 90/00* (2016.01)
*A61B 17/02* (2006.01)
*A61B 18/00* (2006.01)

(52) U.S. Cl.
CPC .... *A61B 17/00234* (2013.01); *A61B 17/0218* (2013.01); *A61B 18/16* (2013.01); *A61B 90/08* (2016.02); *A61B 2017/00287* (2013.01); *A61B 2017/00557* (2013.01); *A61B 2018/00601* (2013.01); *A61B 2018/162* (2013.01); *A61B 2090/0801* (2016.02)

(58) Field of Classification Search
CPC .......... A61B 17/00234; A61B 17/0218; A61B 17/3423; A61B 2017/00287; A61B 2090/0801; A61B 2090/08021; A61B 2018/00601; A61B 2018/162; A61B 2018/142; A61B 2018/00982; A61B 2018/1402; A61B 2017/0225; A61B 2017/00557; A61B 90/08
USPC ........................................................ 606/114
See application file for complete search history.

(56) References Cited

U.S. PATENT DOCUMENTS

| 4,984,564 A | 1/1991 | Yuen |
| 5,007,926 A | 4/1991 | Derbyshire |
| 5,037,379 A | 8/1991 | Clayman et al. |
| 5,078,726 A | 1/1992 | Kreamer |
| 5,143,082 A | 9/1992 | Kindberg et al. |

(Continued)

*Primary Examiner* — Jocelin C Tanner
(74) *Attorney, Agent, or Firm* — Carter, DeLuca & Farrell LLP

(57) ABSTRACT

A kit for extracting a tissue specimen includes a specimen container having a proximal rim and a specimen bag operably supported about the proximal rim and depending therefrom. The specimen bag includes a plurality of ribs depending from the proximal rim having a series of mechanical interfaces associated therewith and extending therealong. The kit also includes a cutting guard having a body with proximal and distal ends. The distal end is configured for insertion within the specimen bag when disposed within an incision and the proximal end defines an opening therein configured to facilitate introduction of one or more surgical instruments therethrough. The cutting guard includes one or mechanical interfaces operably associated with the body of the cutting guard configured to selectively engage one of the series of mechanical interfaces of one of the plurality of ribs of the specimen container upon insertion of the cutting guard within the incision.

8 Claims, 15 Drawing Sheets

(56) References Cited

U.S. PATENT DOCUMENTS

| | | |
|---|---|---|
| 5,159,921 A | 11/1992 | Hoover |
| 5,171,262 A | 12/1992 | MacGregor |
| 5,176,659 A | 1/1993 | Mancini |
| 5,213,114 A | 5/1993 | Bailey, Jr. |
| 5,215,101 A | 6/1993 | Jacobs et al. |
| 5,215,521 A | 6/1993 | Cochran et al. |
| 5,224,930 A | 7/1993 | Spaeth et al. |
| 5,231,974 A | 8/1993 | Giglio et al. |
| 5,308,327 A | 5/1994 | Heaven et al. |
| 5,312,416 A | 5/1994 | Spaeth et al. |
| 5,330,483 A | 7/1994 | Heaven et al. |
| 5,354,303 A | 10/1994 | Spaeth et al. |
| 5,374,272 A | 12/1994 | Arpa et al. |
| 5,380,304 A | 1/1995 | Parker |
| 5,411,549 A | 5/1995 | Peters |
| 5,441,515 A | 8/1995 | Khosravi et al. |
| 5,449,382 A | 9/1995 | Dayton |
| 5,520,610 A | 5/1996 | Giglio et al. |
| 5,578,075 A | 11/1996 | Dayton |
| 5,611,803 A | 3/1997 | Heaven et al. |
| 5,618,296 A | 4/1997 | Sorensen et al. |
| 5,636,639 A | 6/1997 | Turturro et al. |
| 5,649,550 A | 7/1997 | Crook |
| 5,707,385 A | 1/1998 | Williams |
| 5,769,794 A | 6/1998 | Conlan et al. |
| 5,785,677 A | 7/1998 | Auweiler |
| 5,810,721 A | 9/1998 | Mueller et al. |
| 5,814,044 A | 9/1998 | Hooven |
| 5,906,577 A | 5/1999 | Beane et al. |
| 5,957,888 A | 9/1999 | Hinchliffe |
| 5,971,995 A | 10/1999 | Rousseau |
| 5,993,427 A | 11/1999 | Rolland et al. |
| 6,027,779 A | 2/2000 | Campbell et al. |
| 6,039,748 A | 3/2000 | Savage et al. |
| 6,048,309 A | 4/2000 | Flom et al. |
| 6,059,793 A | 5/2000 | Pagedas |
| 6,090,136 A | 7/2000 | McDonald et al. |
| 6,162,172 A | 12/2000 | Cosgrove et al. |
| 6,206,889 B1 | 3/2001 | Bennardo |
| 6,228,095 B1 | 5/2001 | Dennis |
| 6,258,102 B1 | 7/2001 | Pagedas |
| 6,350,267 B1 | 2/2002 | Stefanchik |
| 6,382,211 B1 | 5/2002 | Crook |
| 6,387,102 B2 | 5/2002 | Pagedas |
| 6,406,440 B1 | 6/2002 | Stefanchik |
| 6,814,700 B1 | 11/2004 | Mueller et al. |
| 7,547,310 B2 | 6/2009 | Whitfield |
| 7,670,346 B2 | 3/2010 | Whitfield |
| 7,691,120 B2 | 4/2010 | Shluzas et al. |
| 8,075,567 B2 | 12/2011 | Taylor et al. |
| 8,206,294 B2 | 6/2012 | Widenhouse et al. |
| 8,409,112 B2 | 4/2013 | Wynne et al. |
| 8,409,216 B2 | 4/2013 | Parihar et al. |
| 8,414,596 B2 | 4/2013 | Parihar et al. |
| 8,425,533 B2 | 4/2013 | Parihar et al. |
| 8,540,628 B2 | 9/2013 | O'Prey et al. |
| 8,579,914 B2 | 11/2013 | Menn et al. |
| 8,597,180 B2 | 12/2013 | Copeland et al. |
| 8,740,904 B2 | 6/2014 | Stopek |
| 8,777,849 B2 | 7/2014 | Haig et al. |
| 8,864,658 B2 | 10/2014 | Wilkins et al. |
| 8,961,408 B2 | 2/2015 | Wilkins et al. |
| 8,968,329 B2 | 3/2015 | Cabrera |
| 8,986,321 B2 | 3/2015 | Parihar et al. |
| 9,017,340 B2 | 4/2015 | Davis |
| 9,877,893 B2 | 1/2018 | Taylor et al. |
| 2005/0267492 A1 | 12/2005 | Poncet et al. |
| 2006/0200169 A1 | 9/2006 | Sniffin |
| 2006/0200170 A1 | 9/2006 | Aranyi |
| 2010/0262080 A1* | 10/2010 | Shelton, IV ........ A61B 17/3423 600/206 |
| 2010/0312063 A1* | 12/2010 | Hess ................ A61B 17/3423 600/204 |
| 2010/0312189 A1 | 12/2010 | Shelton, IV et al. |
| 2011/0184311 A1 | 7/2011 | Parihar et al. |
| 2011/0190779 A1 | 8/2011 | Gell et al. |
| 2011/0282237 A1 | 11/2011 | Conlon |
| 2011/0319719 A1 | 12/2011 | O'Prey et al. |
| 2012/0083795 A1 | 4/2012 | Fleming et al. |
| 2012/0157777 A1 | 6/2012 | Okoniewski |
| 2013/0225933 A1* | 8/2013 | Kleyman ............ A61B 17/3423 600/206 |
| 2013/0325025 A1 | 12/2013 | Hathaway et al. |
| 2014/0052018 A1 | 2/2014 | Hawkins |
| 2017/0224321 A1* | 8/2017 | Kessler ............. A61B 17/3211 |

* cited by examiner

FREE STANDING BAG WITH INTEGRATED CUTTING GUARD INTERFACE

BACKGROUND

Technical Field

The present disclosure relates generally to surgical apparatuses for use in minimally invasive surgical procedures, such as endoscopic and/or laparoscopic procedures, and more particularly, the present disclosure relates to a free standing specimen bag with an integrated cutting guard interface for supporting a cutting guard.

Background of Related Art

Minimally invasive surgery, such as endoscopic surgery, reduces the invasiveness of surgical procedures. Endoscopic surgery involves surgery through body walls, for example, viewing and/or operating on the ovaries, uterus, gall bladder, bowels, kidneys, appendix, etc. There are many common endoscopic surgical procedures, including arthroscopy, laparoscopy, gastroentroscopy and laryngobronchoscopy, just to name a few. In these procedures, trocars are utilized for creating incisions through which the endoscopic surgery is performed. Trocar tubes or cannula devices are extended into and left in place in the abdominal wall to provide access for endoscopic surgical tools. A camera or endoscope is inserted through a trocar tube to permit the visual inspection and magnification of the body cavity. The surgeon can then perform diagnostic and/or therapeutic procedures at the surgical site with the aid of specialized instrumentation, such as forceps, graspers, cutters, applicators, and the like, which are designed to fit through additional cannulas. To protect the opening from accidental penetration by the surgical instruments, wound retractors and wound protectors are often placed across the opening.

When removing certain tissues from the body cavity, for example tumor tissue, it is important that the tumor tissue does not come into contact with healthy or uninvolved tissue, so as in this way to avoid metastasis and avoid harming the patient. Minimally invasive surgical procedures, however, may be limited where large size tumors or large masses of tissue have to be removed from a body cavity. If tumor tissue or tissue parts have to be removed, they may be introduced into an "extraction bag," also referred to herein as a "specimen bag," at the site where the tumor or diseased tissue has been detached from the surrounding tissue, after which the specimen bag is withdrawn from the body, normally through a trocar, wound guard or similar device, thereby minimizing contact of the diseased tissue with healthy tissue.

In some instances, depending upon the volume of tissue being removed from the body, the tissue within the specimen bag must be broken up prior to removal from the body to allow for the specimen bag and its contents to pass through the opening used to conduct the endoscopic procedure. In these instances, a cutting mechanism (e.g., electrosurgical cutting tool, mechanical cutting tool, etc.) may be deployed within the surgical cavity and specimen bag to cut excess tissue so that the tissue may be extracted therethrough.

SUMMARY

In accordance with aspects of the present disclosure, a cutting guard for use with a wound retractor includes a body having proximal and distal portions and a body lumen extending therebetween. The body lumen includes a flexible inner peripheral surface extending therethrough, the flexible inner peripheral surface including one or more ground contacts. An elongated ground guard is included having a proximal end defining a proximal opening and a distal end defining a distal opening. The elongated ground guard defines a guard lumen therethrough extending from the proximal opening to the distal opening. The elongated ground guard encapsulating the flexible inner peripheral surface of the body lumen.

A biasing element is disposed at least partially within the guard lumen and encircles the flexible inner peripheral surface of the body lumen. The biasing element biases the flexible inner peripheral surface inwardly. A cutting electrode is disposed proximate the distal opening of the elongated ground guard and is electrically connected to a first potential of an electrical energy source. The proximal end of the ground guard or the ground lumen electrically connects to a second potential of the electrical energy source.

Upon externalizing of tissue through the distal opening of the elongated ground guard, oversized tissue that does not fit through the distal opening of the elongated ground guard forces the flexible inner peripheral surface of the body lumen and the ground contact outwardly to engage the proximal end of the ground guard or the ground lumen to complete an electrical circuit with the cutting electrode to energize the cutting electrode to excise oversized tissue.

In aspects according to the present disclosure, the biasing element is a spring, a living hinge, or a compressible disc. In other aspects according to the present disclosure, the cutting electrode is ring-shaped. In still other aspects according to the present disclosure, the cutting electrode and the distal opening are similar in size and shape. In yet other aspects according to the present disclosure, the cutting electrode is disposed in concentric registration with the distal opening of the ground guard.

In aspects according to the present disclosure, the cutting guard includes one or more mechanical interfaces adapted to securely engage a wound retractor. In other aspects according to the present disclosure, the cutting electrode of the cutting guard is activated only when the ground contact completes the electrical circuit.

In accordance with aspects of the present disclosure, a cutting guard for use with a wound retractor includes a body having proximal and distal portions and a body lumen extending therebetween. The body lumen includes a flexible inner peripheral surface extending therethrough. An elongated ground guard is included having proximal end defining a proximal opening and a distal end defining a distal opening. The elongated ground guard defines a guard lumen therethrough extending from the proximal opening to the distal opening, the elongated ground guard encapsulating the flexible inner peripheral surface of the body lumen.

A biasing element is disposed at least partially within the guard lumen and encircles the flexible inner peripheral surface of the body lumen. The biasing element biases the flexible inner peripheral surface inwardly.

A cutting electrode is disposed proximate the distal opening of the elongated ground guard and electrically connects to a first potential of an electrical energy source. The proximal end of the ground guard or the ground lumen electrically connects to a second potential of the electrical energy source.

Upon externalizing of tissue through the distal opening of the elongated ground guard, oversized tissue that does not fit through the distal opening of the elongated ground guard forces the flexible inner peripheral surface of the body lumen and the biasing element outwardly to engage the proximal end of the ground guard or the ground lumen to complete an electrical circuit with the cutting electrode to energize the cutting electrode to excise oversized tissue.

In aspects according to the present disclosure, the biasing element is a spring, a living hinge, or a compressible disc. In other aspects according to the present disclosure, the cutting electrode is ring-shaped. In still other aspects according to the present disclosure, the cutting electrode and the distal opening are similar in size and shape. In yet other aspects according to the present disclosure, the cutting electrode is disposed in concentric registration with the distal opening of the ground guard.

In aspects according to the present disclosure, the cutting guard includes one or more mechanical interfaces adapted to securely engage a wound retractor. In other aspects according to the present disclosure, the cutting electrode of the cutting guard is activated only when the biasing element completes the electrical circuit.

In accordance with aspects of the present disclosure, a cutting guard for use with a specimen container includes a body have proximal and distal ends. The distal end is configured for insertion within a specimen container when disposed within an incision. The proximal end defines an opening therein configured to facilitate introduction of one or more surgical instruments therethrough. One or more mechanical interfaces are operably associated with the body of the cutting guard and are configured to selectively engage a corresponding one or more mechanical interfaces operably associated with the specimen container upon insertion of the cutting guard within the incision.

In aspects according to the present disclosure, the one or more mechanical interfaces of the cutting guard include a projecting finger that is configured to engage a corresponding mechanical interface of the specimen container as the cutting guard is inserted into the incision. In other aspects according to the present disclosure, the shape of the cutting guard is frustoconical to bias the one or more mechanical interfaces of the cutting guard into engagement with a corresponding mechanical interface of the specimen container when the cutting guard is inserted within the incision. In still other aspects according to the present disclosure, the cutting guard includes a plurality of projecting fingers configured to selectively engage a corresponding plurality of the mechanical interfaces associated with the specimen container.

In accordance with aspects of the present disclosure, a kit for extracting a tissue specimen includes a specimen container having: a proximal rim; a specimen bag operably supported about the proximal rim and depending therefrom, the proximal rim and the specimen bag defining an internal cavity therein; and a plurality of ribs depending from the proximal rim including a series of mechanical interfaces associated therewith and extending therealong. The kit also has a cutting guard that includes: a body have proximal and distal ends, the distal end configured for insertion within the specimen container when disposed within an incision, and the proximal end defining an opening therein configured to facilitate introduction of one or more surgical instruments therethrough; and one or more mechanical interfaces operably associated with the body of the cutting guard and configured to selectively engage one of the series of mechanical interfaces of one of the plurality of ribs of the specimen container upon insertion of the cutting guard within the incision.

In aspects according to the present disclosure, one or more of the mechanical interfaces of the cutting guard includes a projecting finger that is configured to engage one of the corresponding series of mechanical interfaces of one of the plurality of ribs of the specimen container as the cutting guard is inserted into the incision. In other aspects according to the present disclosure, the shape of the cutting guard is frustoconical to bias the one or more mechanical interfaces of the cutting guard into engagement with a corresponding one of the series of mechanical interfaces of one of the plurality of ribs of the specimen container when the cutting guard is inserted within the incision.

In aspects according to the present disclosure, the cutting guard includes a plurality of projecting fingers, each finger of the plurality of fingers configured to selectively engage a corresponding one of the series of the mechanical interfaces associated with each rib of the specimen container.

In aspects according to the present disclosure, the plurality of ribs are disposed in an array-like fashion about an inner periphery of the specimen bag. In other aspects according to the present disclosure, the cutting guard includes a plurality of mechanical interfaces disposed in an array-like fashion about the proximal end thereof. In still other aspects according to the present disclosure, the cutting guard includes a plurality of mechanical interfaces disposed in an array-like fashion about the proximal end thereof. The plurality of mechanical interfaces of the cutting guard is disposed in registration with the plurality of ribs of the specimen container such that, upon insertion into the incision, each of the plurality of mechanical interfaces of the cutting guard can selectively engage one of the corresponding series of mechanical interfaces of the plurality of ribs of the specimen container.

In aspects according to the present disclosure, the specimen bag is configured to be furled about the proximal rim to facilitate externalization of a tissue specimen.

BRIEF DESCRIPTION OF THE DRAWINGS

Various embodiments of the presently disclosed wound retractor and specimen bag assembly are described herein with reference to the drawings wherein.

DETAILED DESCRIPTION

Figure 1B:
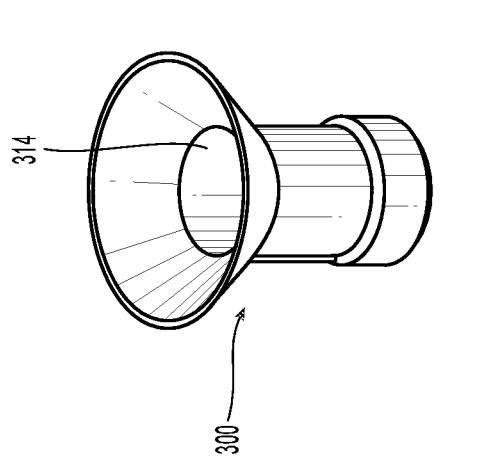
FIG. 1B is a perspective view of a wound guard for use with the wound retractor and specimen bag.
Figure 1A:
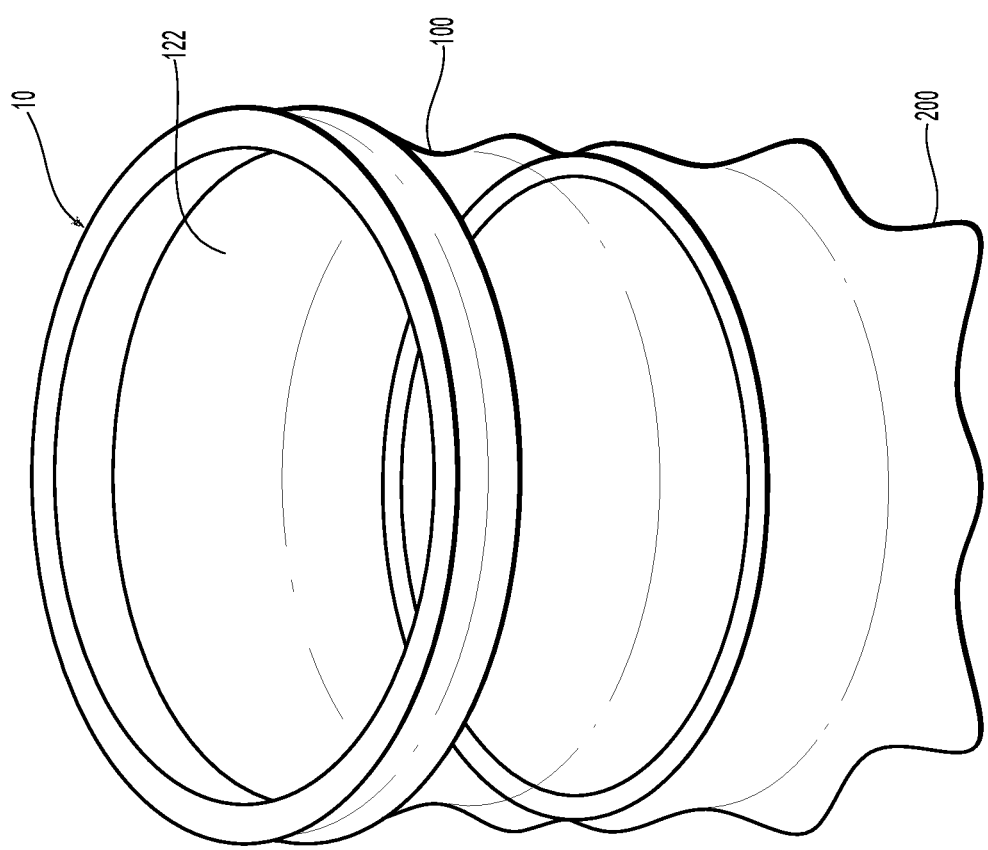
FIG. 1A is a perspective view of a prior art wound retractor and specimen bag shown assembled.
Figure 2:
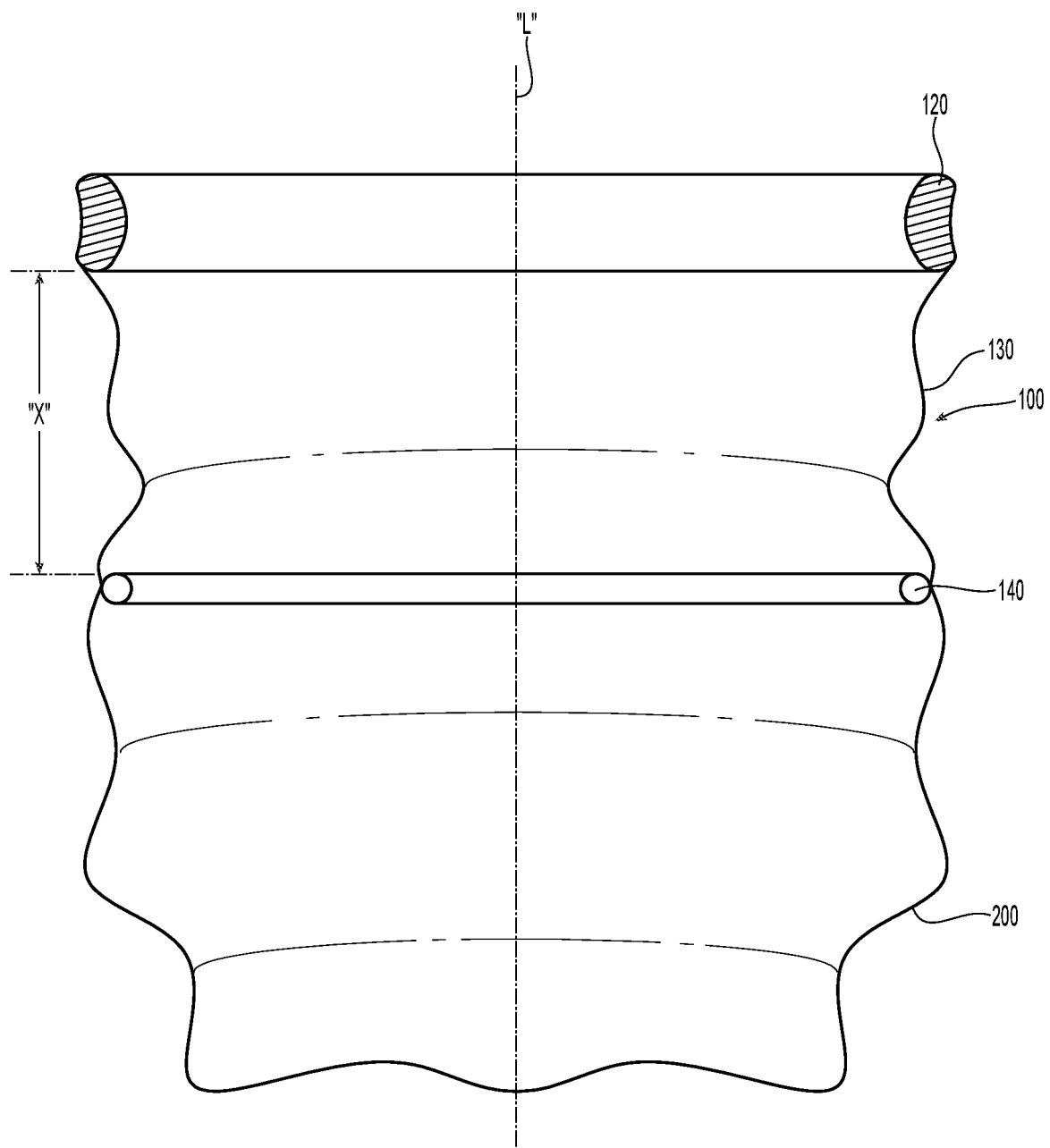
FIG. 2 is a perspective view of the prior art specimen bag and wound retractor shown in FIG. 1.
Figure 3A:
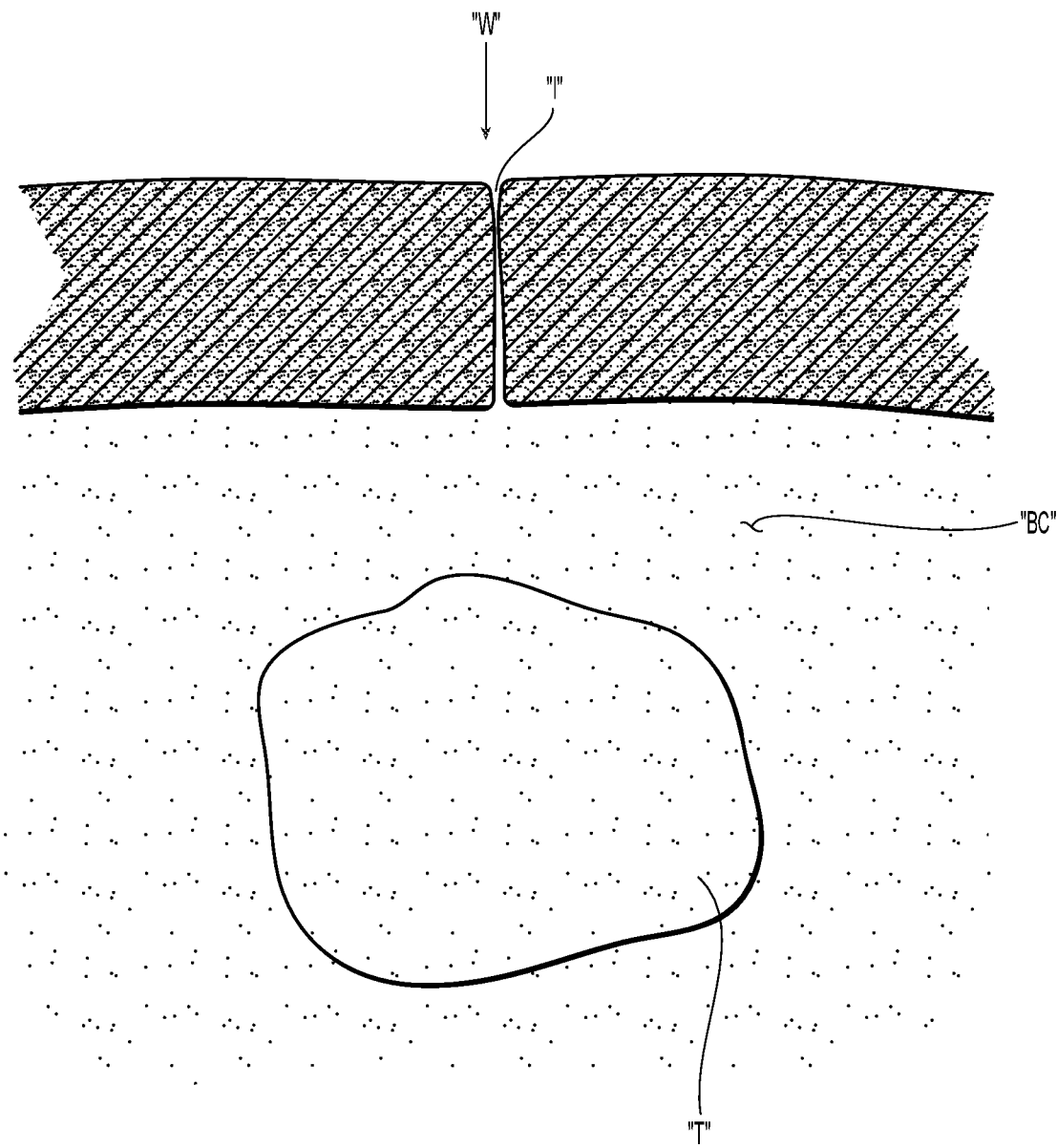
FIG. 3A is a cross-sectional view of a patient's body, showing a wound, incision, and tissue specimen to be removed from a body cavity.
Figure 3B:
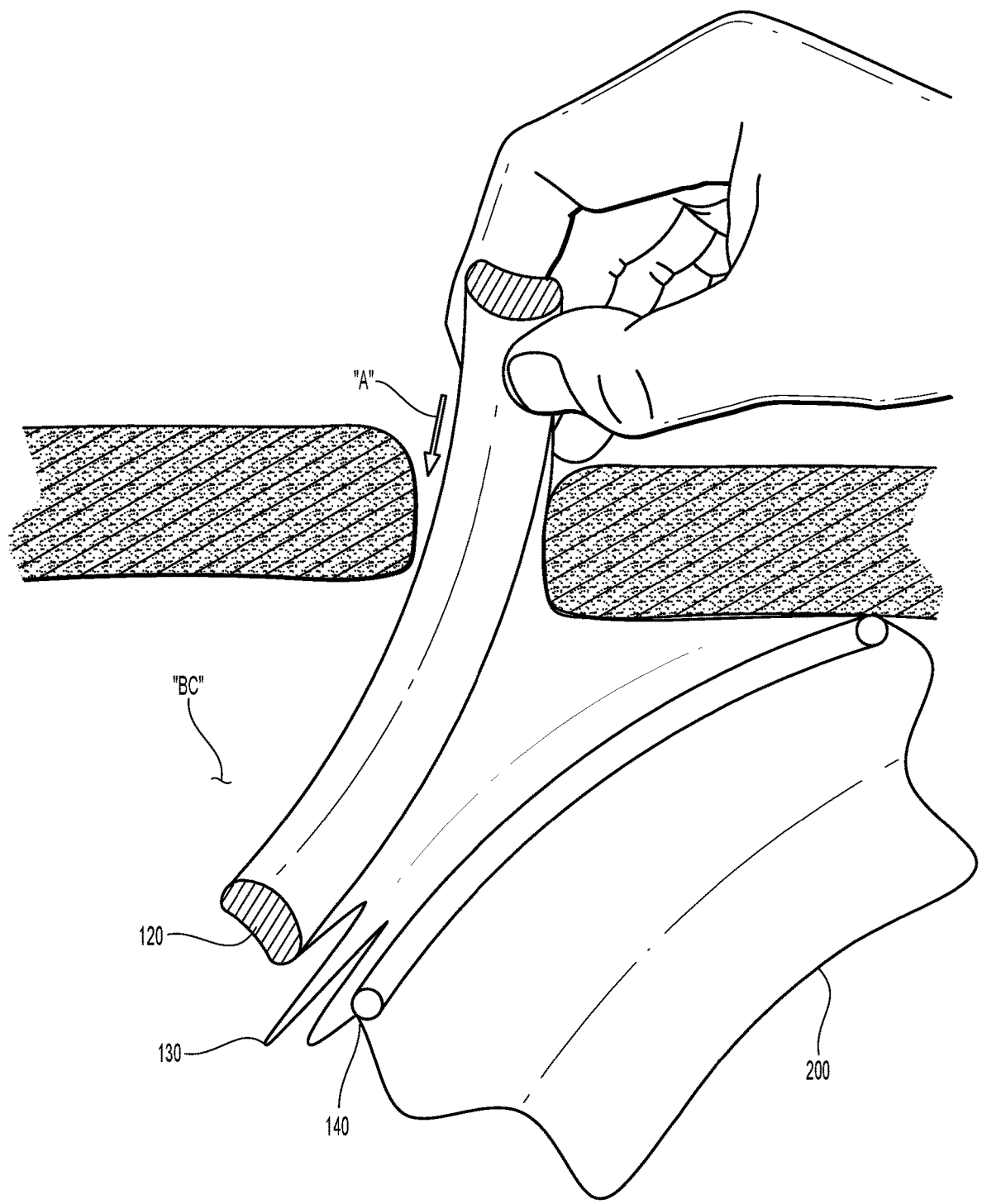
FIG. 3B is a perspective, partial cross-sectional view showing the insertion of the wound retractor and specimen bag in FIG. 2 into the body cavity through the incision.
Figure 3C:
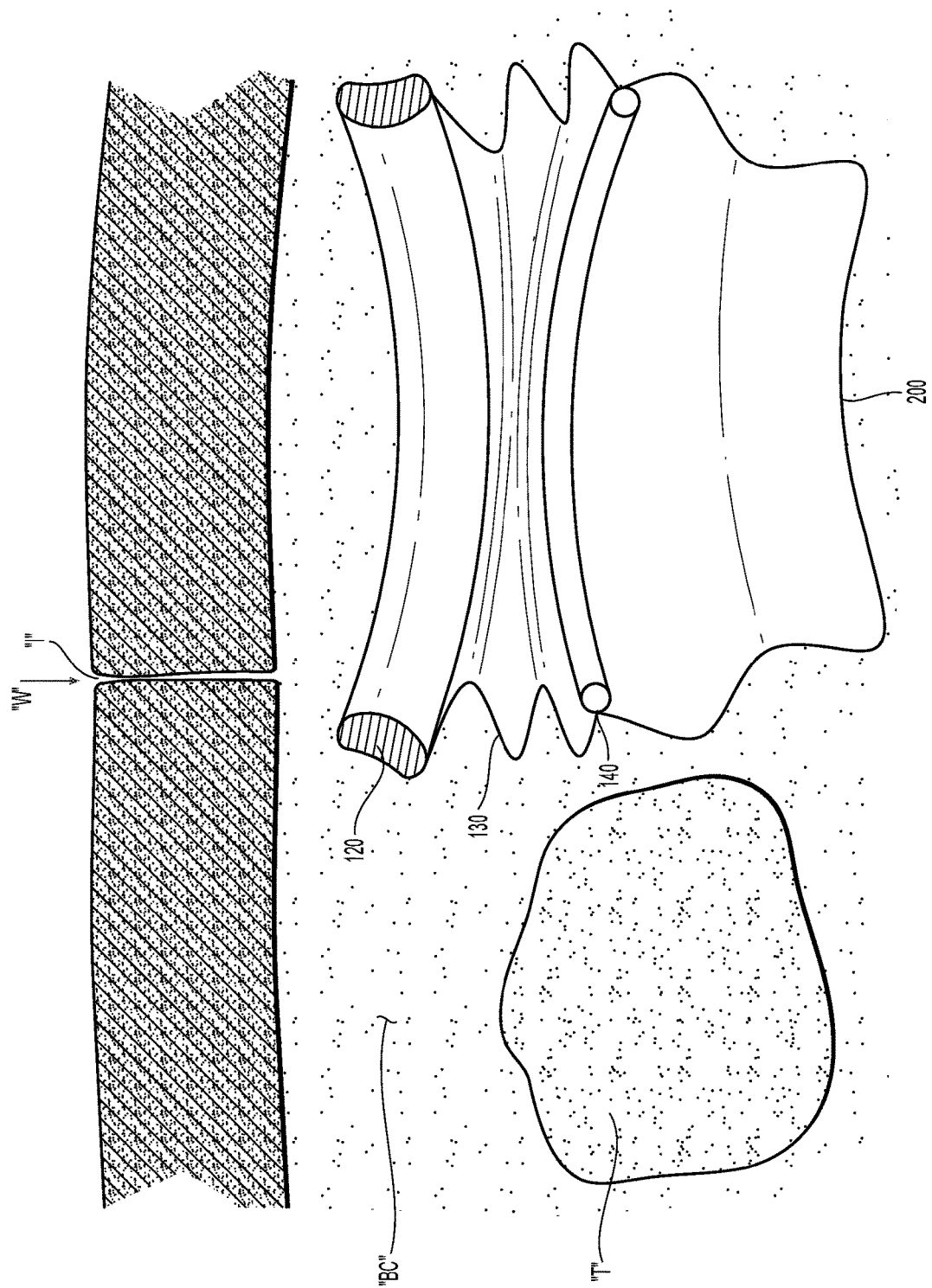
FIG. 3C is a perspective view of the wound retractor and specimen bag shown in FIG. 2 in the body cavity, adjacent tissue to be removed from the body cavity.
Figure 3D:
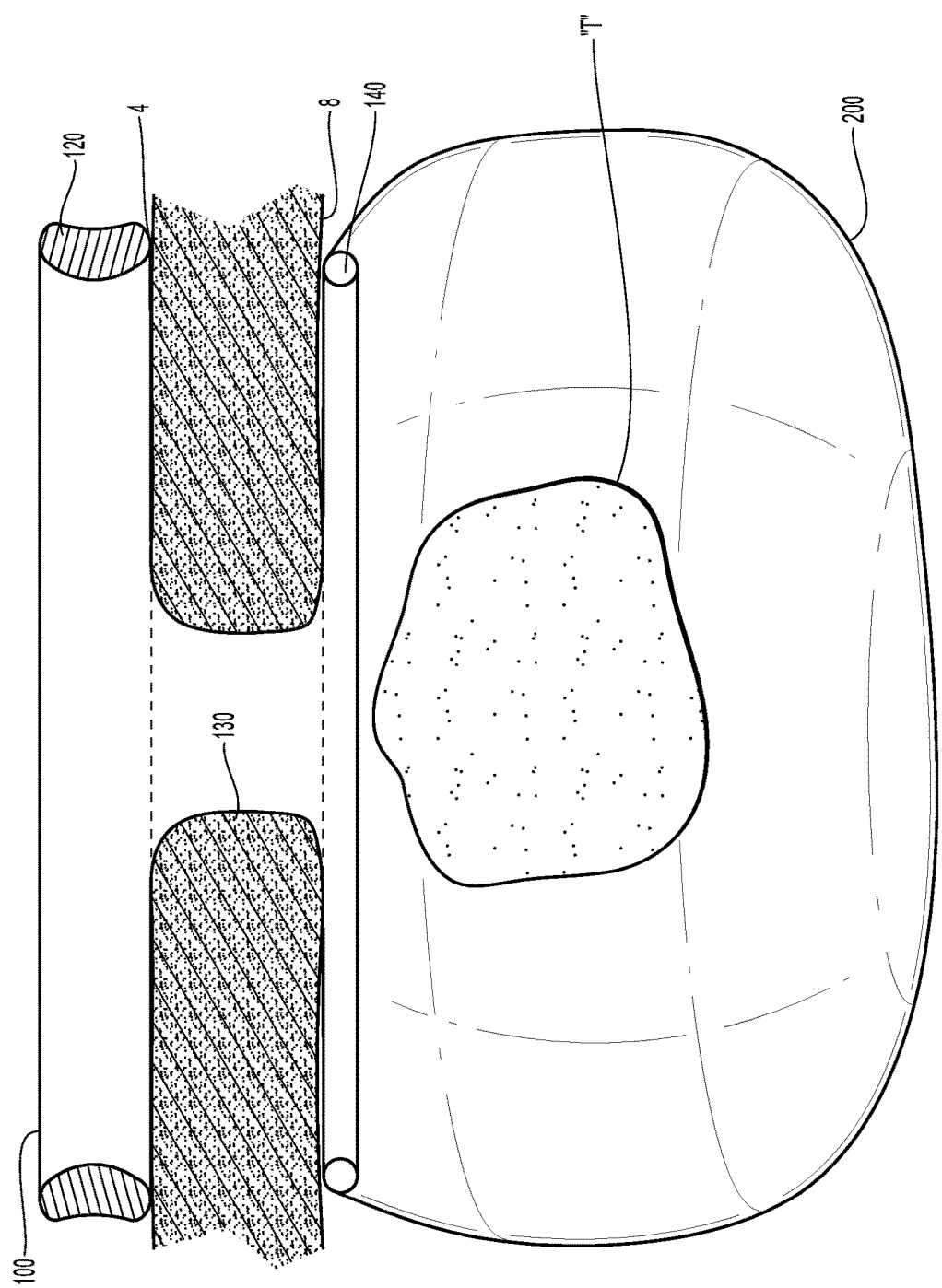
FIG. 3D is a perspective view of the wound retractor and specimen bag shown in FIG. 2 inserted into the incision and the specimen bag positioned within the body cavity.
Figure 4:
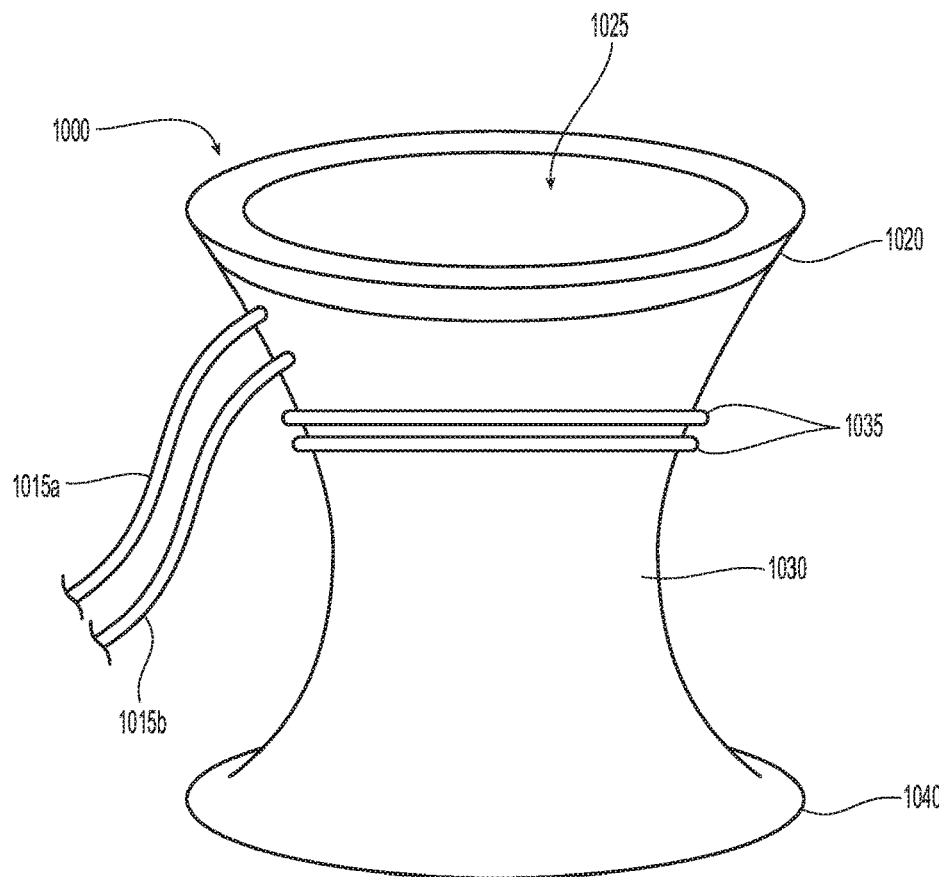
FIG. 4 is a perspective view of a wound retractor in accordance with the present disclosure.
Figure 5:
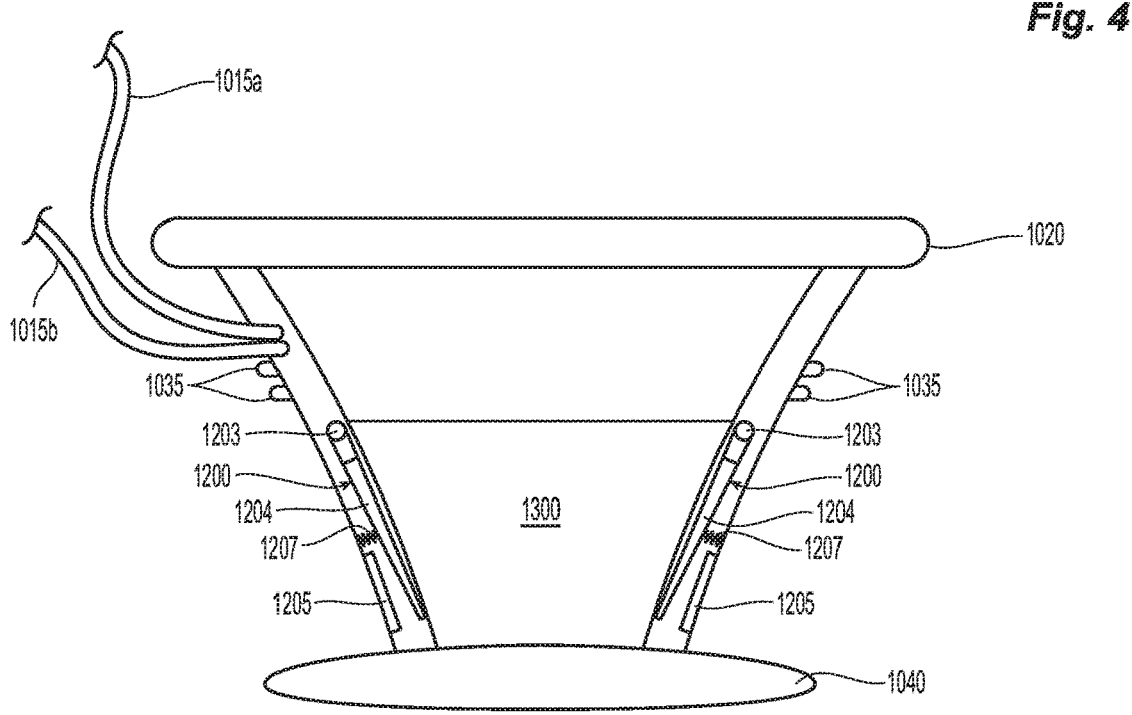
FIG. 5 is an internal view of the wound retractor of FIG. 4.
Figure 6A:
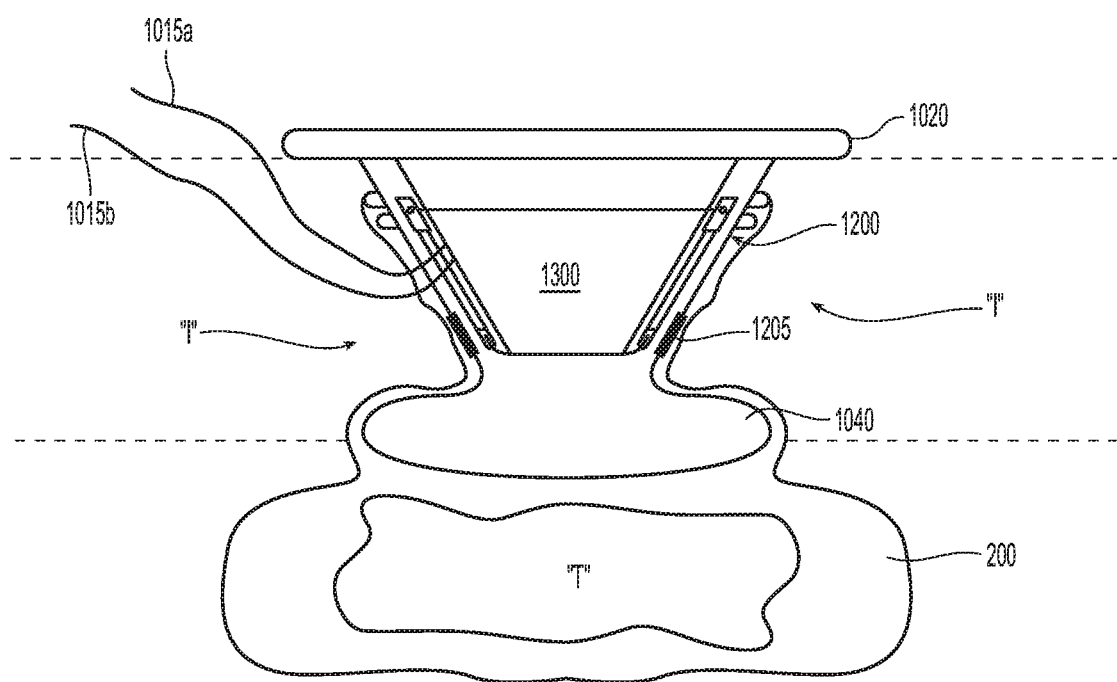
FIG. 6A is an internal view of the wound retractor of FIG. 4 shown within the incision with a tissue specimen disposed within a specimen bag for externalization.
Figure 6B:
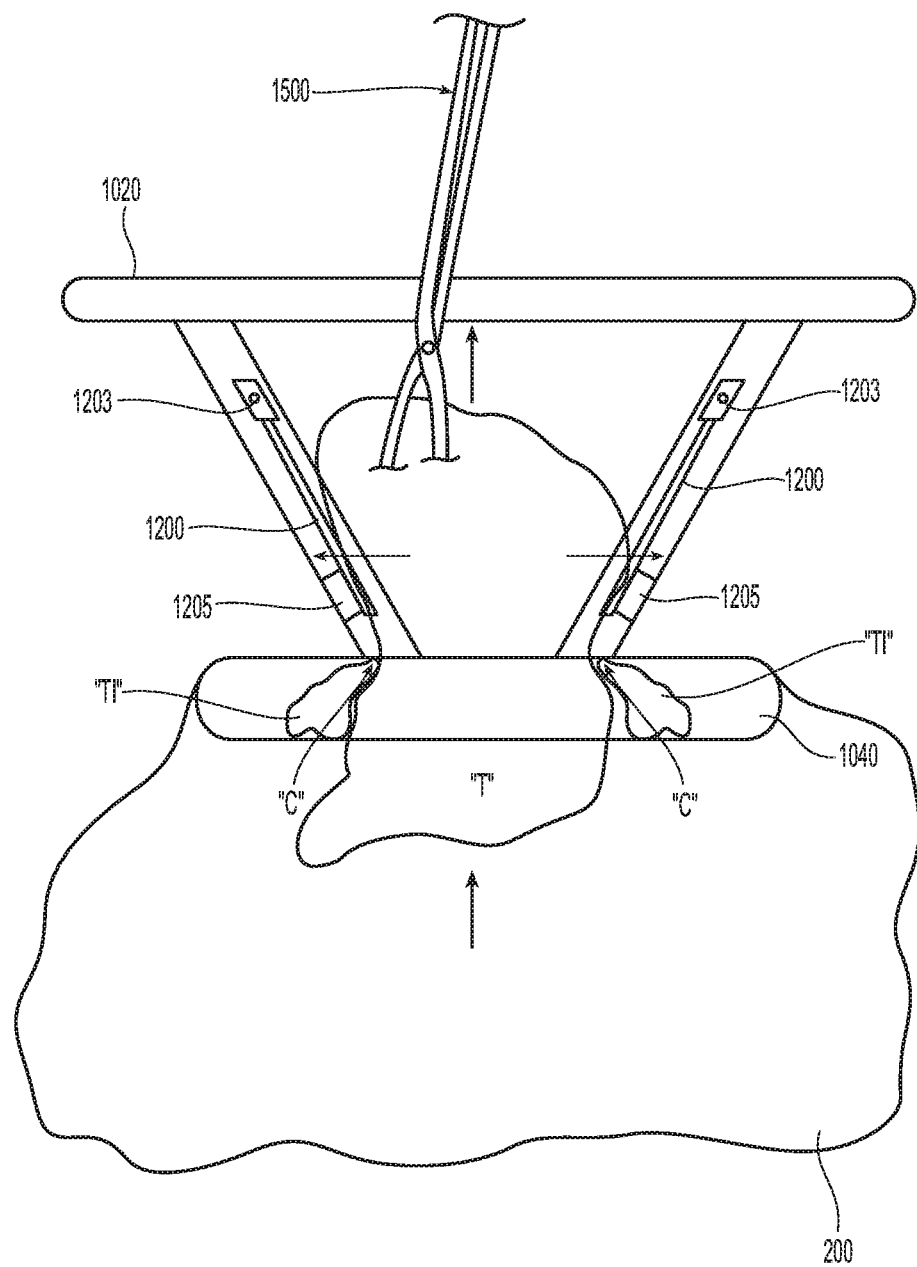
FIG. 6B is an internal view of the wound retractor of FIG. 4 shown within the incision with the tissue specimen being externalized through the wound retractor with a forceps and oversized tissue being excised.
Figure 7A:
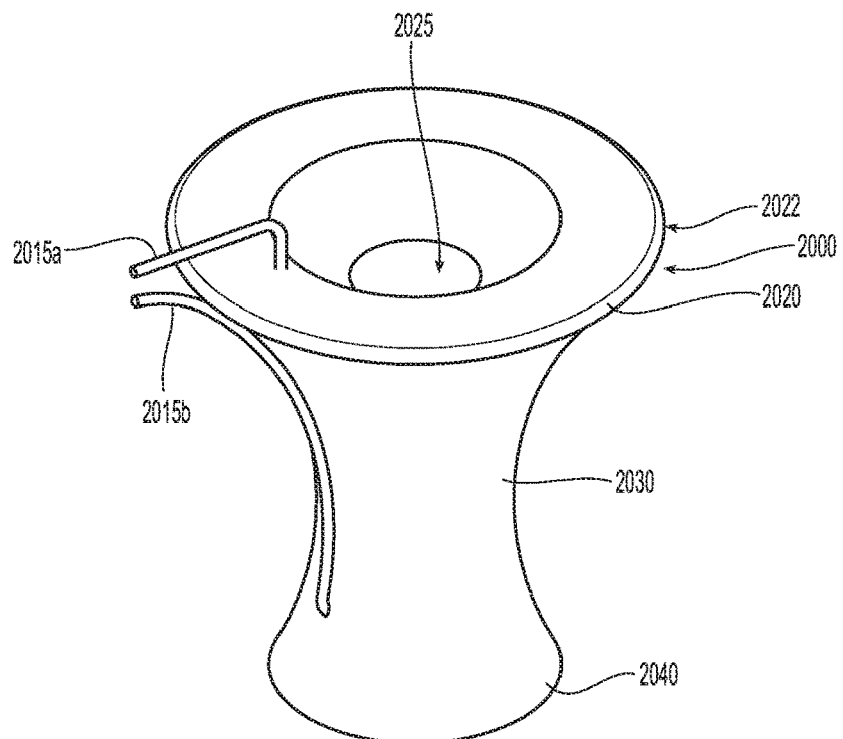
FIGS. 7A-7E are varying views of a cutting guard for use with a wound retractor in accordance with another embodiment of the present disclosure.
Figure 7B:
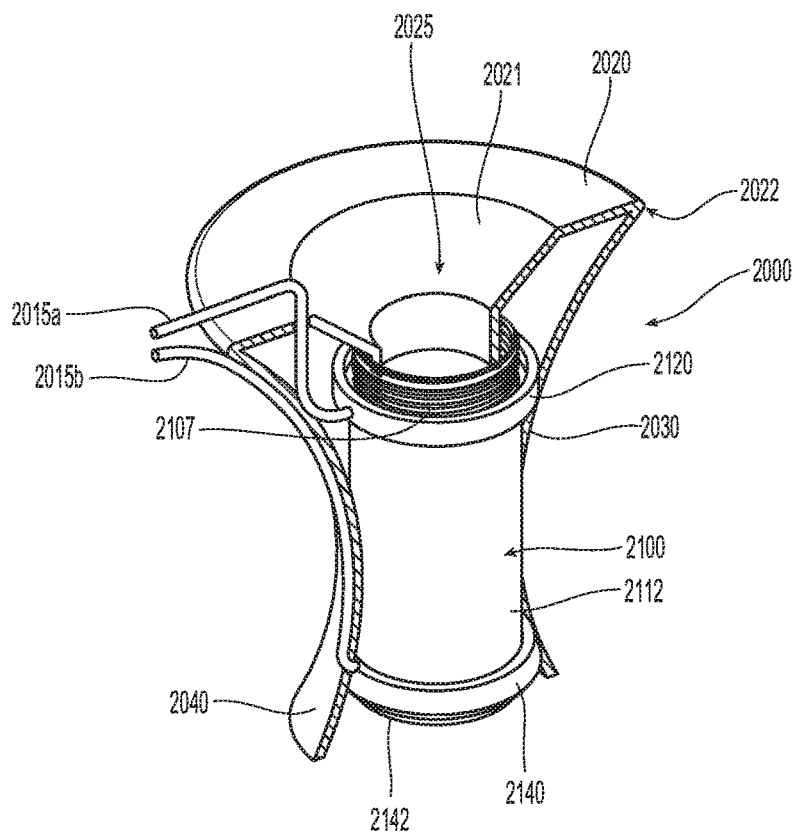
Figure 7C:
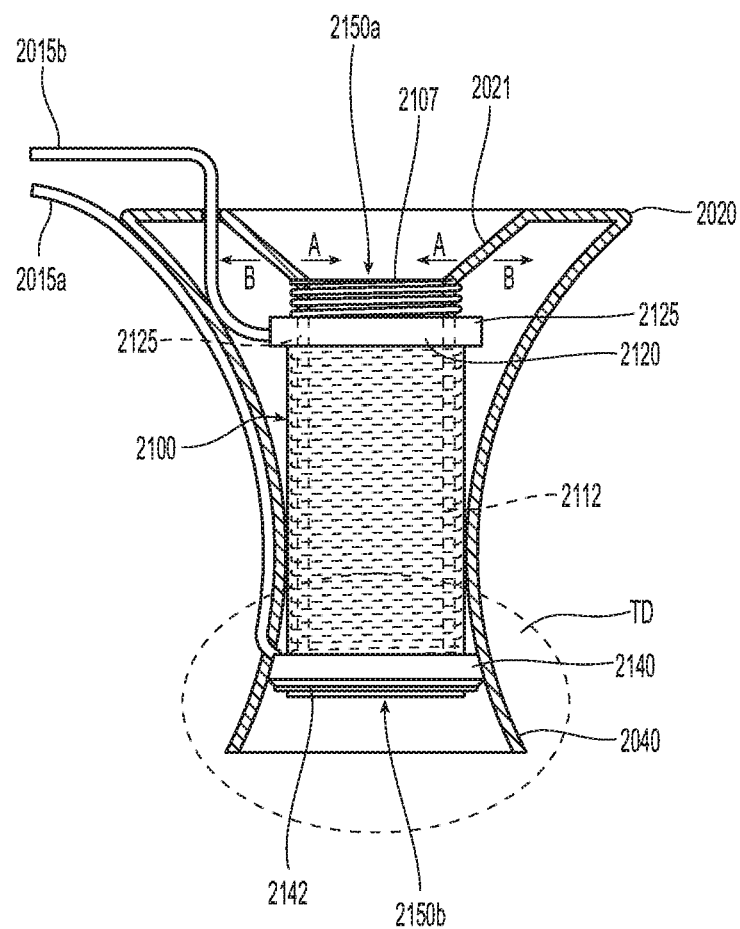
Figure 7D:
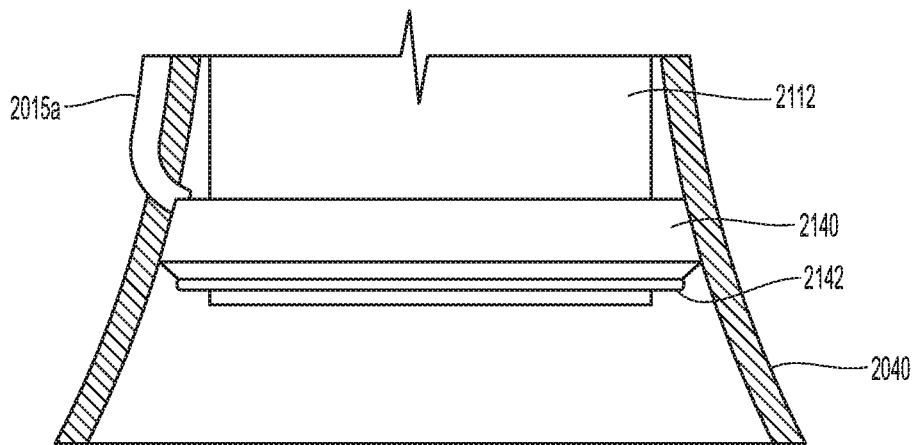
Figure 7E:
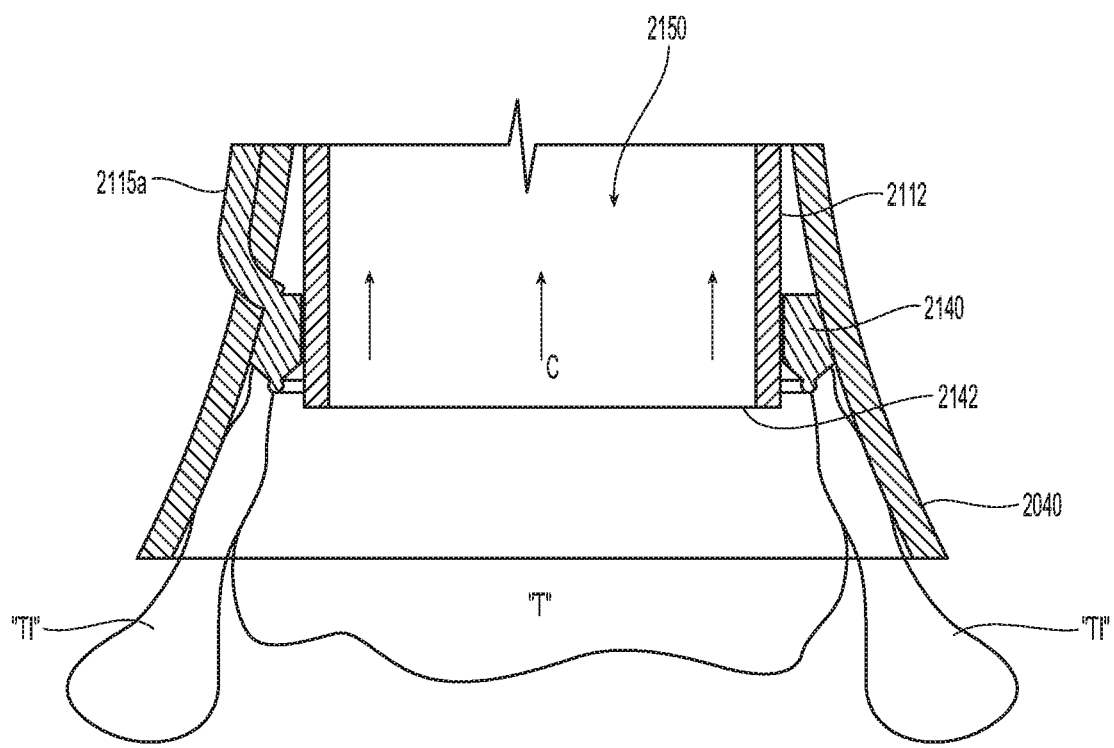

The present disclosure provides a cutting guard or wound retractor with radiofrequency (RF) capabilities and that is selectively engageable with a wound retractor and specimen bag for use in minimally invasive surgical procedures. As used herein with reference to the present disclosure, minimally invasive surgical procedures encompass laparoscopic procedures and endoscopic procedures, and refer to procedures utilizing scopes or similar devices having relatively narrow operating portions or a small incision in the skin.

The aspects of the present disclosure may be modified for use with various methods for retrieving tissue specimens during minimally invasive surgical procedures, sometimes referred to herein as minimally invasive procedures. Examples of minimally invasive procedures include, for example, cholecystectomies, appendectomies, nephrectomies, colectomies, splenectomies, and the like.

As used herein, the term distal refers to the portion of a surgical apparatus, including a wound retractor and specimen bag of the present disclosure, which is farthest from the user, while the term proximal refers to that portion of the surgical apparatus of the present disclosure which is closest to the user.

Typically a wound retractor includes various mechanical interfaces for mounting a specimen bag thereto or a specimen bag is integrally associated therewith. A wound retractor or cutting guard (as explained in more detail below with reference to the present disclosure) is configured to mount within or securely engage the wound retractor.

The wound retractor itself typically includes a sleeve member having at least two rings, including a proximal ring and a distal ring, with a film extending between the two rings. The specimen bag component is typically attached proximate the distal ring of the wound retractor. In use, the entire surgical apparatus is passed through an incision and placed within a body cavity, and tissue to be removed therefrom, referred to in embodiments as a "tissue specimen", is passed through the wound retractor component and placed within the specimen bag. The proximal ring of the wound retractor component is then removed from the body cavity and placed adjacent the skin on the outside of the body adjacent the incision, with the distal ring of the sleeve member and specimen bag remaining within the body, so that the film extends through the incision and is adjacent the tissue encompassing the incision into the body. The wound guard protects the patient during morcellation of tissue with a scalpel or some other morcellation device as the tissue is removed from the specimen bag. The present disclosure incorporates a RF dissection tool to aid in morcellation of the specimen sample as the sample is being extracted from the surgical cavity and specimen bag through a cutting guard.

Embodiments of the present disclosure will now be described in detail with reference to the drawings, in which like reference numerals designate identical or corresponding elements in each of the several views. In the following description, well-known functions or constructions are not described in detail to avoid obscuring the present disclosure in unnecessary detail.

FIGS. 1A-3D illustrate a typical prior art wound retractor 10 for use with a wound guard 300 and a specimen bag 200. The wound retractor 10 and specimen bag 200 are adapted for insertion into a wound "W" through an incision "I" (as illustrated in FIG. 3). The incision "I" may be a single incision, e.g., through the abdominal or peritoneal lining, or a naturally occurring orifice (i.e. mouth, anus, or vagina).

The wound retractor 100 includes a proximal ring 120, a distal ring 140, and a generally cylindrical film 130 disposed therebetween. The wound retractor 100 and specimen bag 200 further define a longitudinal axis "L" shared by the proximal ring 120, the distal ring 140, and the film 130, as well as the specimen bag 200. The proximal ring 120 and the distal ring 140 may each be detachably coupled or permanently attached to a proximal end portion 132 and a distal end portion 134, respectively, of the film 130 by any means within the purview of those skilled in the art, e.g., glue, suture, impulse welding, chemical or mechanical bonding, an over molding process, etc. In some embodiments, the proximal ring 120, film 130, and distal ring 140 are monolithically integrated such that the wound retractor 100 is a unitary structure.

The proximal ring 120 and the distal ring 140 are axially aligned along longitudinal axis "L" with the film 130 disposed therebetween, as noted above. The proximal ring 120 has a generally circular configuration that defines a circular opening 122 (see FIG. 1A) and is rollable, such that the proximal ring 120 can be rolled towards or away from the distal ring 140 along the longitudinal axis "L", which results in the film 130 being furled or unfurled about the proximal ring 120. The distal ring 140 also has a generally circular configuration that defines a generally circular opening (not shown).

The proximal ring 120 and the distal ring 140 may be fabricated from resilient materials such that the proximal ring 120 and the distal ring 140 may temporarily deform into a generally oblong configuration during insertion of the wound retractor 100 through an incision "I" while reverting to a generally circular configuration during use. For example, thermoplastic polyurethanes sold under the name PELLETHANE®, offers flexibility and a wide range of hardnesses. The proximal ring 120, for example, may be fabricated from PELLETHANE® 2363-80A, PELLETHANE® 2363-90A, a 50/50 composition of PELLETHANE® 2363-80A and PELLETHANE® 2363-90A, or any alternatives known in the art. The distal ring 140 may be fabricated from, for example, PELLETHANE® 2363-90A for the extra small and small size, PELLETHANE® 2363-55D for the medium and large size, a 50/50 composition of PELLETHANE® 2363-90A and PELLETHANE® 2363-55D for the large size, or any alternatives within the purview of those skilled in the art. The proximal ring 120 and the distal ring 140 may be fabricated from the same or different materials.

The film 130 defines a generally cylindrical shape to form a lumen between the proximal ring 120 and the distal ring 140. The circular configuration of the proximal and distal rings 120 and 140, respectively, maintains the film 130 in an expanded state to maintain the lumen in a non-collapsed state. The length "X" between the proximal ring 120 and the distal ring 140 is adjustable. More specifically, the length "X" can be decreased by rolling the proximal ring 120 towards the distal ring 140 to furl the film 130 about the proximal ring 120. Similarly, the length "X" can be increased by rolling the proximal ring 120 away from the distal ring 140 to unfurl the film 130 from about the proximal ring 120. As discussed above, as the proximal ring 120 is rolled towards or away from the distal ring 140, the film 130 furls or unfurls about the proximal ring 120. It should be appreciated that as the film 130 is furled about the proximal ring 120, it reduces the length "X" of the film 130, so the tension in the film between the proximal ring 120 and distal ring 140 is increased to provide a radially outward force within the incision "I".

Typical specimen bags 200 are made of flexible and durable materials within the purview of those skilled in the art, in embodiments, polymeric materials. The specimen bags 200 are capable of allowing a surgeon to introduce cutting devices into the specimen bag to reduce the size of the tissue specimen therein being extracted, thereby facilitating removal of the specimen bag 200 or the specimen from the body. Materials used to form the specimen bags are antistatic, pyrogen-free, non-toxic and sterilizable.

Both the proximal ring 120 and the distal ring 140 may be collapsed from the generally circular configuration to a generally oblong configuration (not shown) for insertion, along with the specimen bag 200, through incision "I". More specifically, as the practitioner squeezes opposing sides of the proximal ring 120 and the distal ring 140 radially inwards, the generally circular openings of the proximal ring 120 and the distal ring 140 are deformed from the generally circular configuration to a generally oblong configuration (not shown) such that the proximal ring 120 and the distal ring 140 assume a smaller profile for ease of insertion through incision "I". Once inserted, the practitioner releases the proximal ring 120 and distal ring 140 and the resiliency of the material urges the proximal ring 120 and the distal ring 140 towards their generally circular configurations.

In embodiments, where the tissue specimen "T" within the specimen bag 200 is too large to pass through the wound retractor 100, tissue is typically broken up by a scalpel, a morcellator, or a similar device to facilitate removal of the tissue specimen "T" from the specimen bag 200. However, while using these instruments, the surgeon needs to remain mindful so as not to damage the specimen bag and prevent resected tissue from entering into a body cavity, e.g., the abdominal cavity. Typically in these instances, a wound guard 300 (FIG. 1B) is introduced within the wound retractor 100 to protect the wound retractor 100 and specimen bag 200 during tissue resection.

The wound guard 300 may be formed of hard, rigid materials. Suitable materials for forming the wound guard 300 include, for example, polyolefins such as polyethylene (including ultra high molecular weight polyethylene) and polypropylene including atactic, isotactic, syndiotactic, and blends thereof; polyethylene glycols (PEGs); polyethylene oxides; copolymers of polyethylene and polypropylene; polyisobutylene and ethylene-alpha olefin copolymers; fluorinated polyolefins such as fluoroethylenes, fluoropropylenes, fluoroPEGs, and polytetrafluoroethylene; polyamides; polyamines; polyimines; polyesters such as polyethylene terephthalate, polyethylene naphthalate, polytrimethylene terephthalate, and polybutylene terephthalate; polyethers; polybutester; polytetramethylene ether glycol; 1,4-butanediol; polyurethanes; acrylic polymers; methacrylics; vinyl halide polymers and copolymers such as polyvinyl chloride; polyvinyl alcohols; polyvinyl ethers such as polyvinyl methyl ether; polyvinylidene halides such as polyvinylidene fluoride and polyvinylidene chloride; polychlorofluoroethylene; polyacrylonitrile; polyaryletherketones; polyvinyl ketones; polyvinyl aromatics such as polystyrene; polyvinyl esters such as polyvinyl acetate; copolymers of vinyl monomers with each other and olefins such as ethylene-methyl methacrylate copolymers; acrylonitrile-styrene copolymers; acrylonitrile butadiene styrene resins; ethylene-vinyl acetate copolymers; alkyd resins; polycarbonates; polyoxymethylenes; polyphosphazines; polyimides; epoxy resins; aramids; silicones; and copolymers and combinations thereof.

The wound guard 300 is typically anchored or otherwise secured to the wound retractor when disposed within the incision, e.g., an inflation port (not shown) may introduce inflation gases into an anchoring balloon located at the distal portion of the wound guard 300. Other common anchoring methods are also envisioned.

With reference to FIGS. 3A-3D, in order to access a tissue specimen "T" positioned within a body cavity "BC" (FIG. 3A), the surgeon first collapses and deforms the proximal ring 120 and the distal ring 140 of the wound retractor 100 into an oblong configuration for insertion into wound "W" through incision "I". Once the wound retractor 100 and the specimen bag 200 are placed through incision "I" and the proximal ring 120 and the distal ring 140 are released, the proximal ring 120 and distal ring 140 resume their generally circular configuration adjacent the tissue specimen "T" to be removed from the body cavity. The surgeon can then introduce tissue specimen "T" through the proximal ring 120, the film 130, and the distal ring 140 into the specimen bag 200 by use of a forceps, grasper, or any other suitable medical device.

Once tissue specimen "T" has been introduced into the specimen bag 200, the surgeon then collapses and deforms the proximal ring 120 using a forceps, grasper, or similar instrument and withdraws the proximal ring 120 through the incision "I". The proximal ring 120 is removed from the body cavity through incision "I" so that it rests on the outer skin 4 adjacent incision "I" and the surgeon adjusts the film 130 and the proximal ring 120, e.g., pulling the proximal ring 120 proximally to tension the film 130, such that the distal ring 140 comes into abutment with an inner surface 8 of wound "W". The distal ring 140 is positioned adjacent the inner surface 8 of wound "W", and reverts to its generally circular configuration so that the generally circular opening of distal ring 140 encompasses the inner surface 8 of the wound "W". With the distal ring 140 in abutment with the inner surface 8 of wound "W", the proximal ring 120 is rolled distally towards the distal ring 140 and the outer surface 4 of wound "W" to a desired position, such that the film 130 is furled about the proximal ring 120 (not shown) and thereby tensioned.

Once the wound retractor 100 and the specimen bag 200 are in position, surgical tools and instruments are typically passed through the wound retractor 100 with the distal ring 140 in abutment to the inner surface 8 of wound "W", and the proximal ring 120 rolled to a desired position and/or brought into abutment to the outer surface 4 of wound "W". The wound retractor 100 may be tensioned further to provide retraction of incision "I", increasing the incision diameter. As typical with prior art devices, if the tissue specimen "T" in the specimen bag 200 is too large to be removed through the incision "I", a wound guard 300 (FIG. 1B), would be introduced through the wound retractor 100. A forceps, or any other grasper device, would then pass through the wound guard 300 into the specimen bag 200 and grasp the tissue specimen "T" therein. To the extent the tissue specimen "T" is too large to pass through the lumen of the wound guard 300, the rigid, hard materials utilized to form the wound guard 300 make it safe to use of morcellators, scalpels, knives, or similar devices to break up the tissue specimen "T" without damaging the wound retractor 100 and/or any body tissue encompassing the incision "I".

The cut portions of the tissue specimen "T" would then be passed through a lumen 314 of the wound guard 300 as it is removed from the specimen bag 200. If the tissue specimen "T" to be removed separates and portions thereof remain in the specimen bag 200 as tissue specimen "T" is cut, the surgeon may grab those additional pieces of tissue with a forceps or other grasper, and/or use a vacuum source for removal of any remaining portion of the tissue specimen "T" from the specimen bag 200. The volume of the tissue specimen "T" in the specimen bag 200, as well as any fluids from the tissue specimen "T", may be reduced to a point that specimen bag 200, with any remaining tissue and/or fluids therein, may pass through incision "I" without need for any further morcellation.

FIGS. 4-6B show a wound retractor 1000 according to the present disclosure including proximal and distal rings 1020 and 1040, respectively, for positioning on either side of an incision "I". Similar to the above-noted prior art rings 120 and 140, rings 1020 and 1040 may be made from any known type of flexible material that is deformable for insertion within an incision and reformable to anchor the wound retractor 1000 therein. Either or both rings 1020 and 1040 may be deformable or, in some instances when the proximal ring 1020 is externalized, only the distal ring 1040 is deformable.

Wound retractor 1000 also includes a series of mechanical interfaces, e.g., ribs 1035, disposed on an outer periphery thereof that are configured to selectively engage and secure a specimen bag 200 thereto. Specimen bag 200 may include complementary mechanical interfaces (not shown) to facilitate secure engagement to the wound retractor 1000. The ribs 1035 are disposed between the proximal and distal rings 1020, 1040 and are engageable with the specimen bag 200 prior to or after insertion of the specimen bag 200 within the incision. For example, the specimen bag 200 may be inserted into the incision "I" to encapsulate the tissue specimen "T" and then secured to the wound retractor 1000 externally (See FIG. 6A). The distal ring 1040 and the specimen bag 200 are then inserted into the incision "I" and the distal ring 1040 expands to secure the wound retractor 1000 therein. Alternatively, in some instances both the wound retractor 1000 and the specimen bag 200 may be inserted into the incision "I" and the wound retractor 1000 is engaged in situ with the specimen bag 200. The proximal ring 1020 is then externalized.

Wound retractor 1000 also includes first and second leads 1015a and 1015b, respectively, that operably and electrically engage the wound retractor 1000 to allow selective application of radiofrequency (RF) energy thereto. More specifically, first lead 1015a connects to the cutting edge "C" disposed proximate the distal-most edge of the wound retractor 1000 (See FIG. 6B) while second lead 1015b connects to a ground contact ring 1205 (or a series of ground contacts (not shown)). Cutting edge "C" may be a wire or simply an edge of an inner cuff 1300 that is disposed between the proximal and distal rings 1020, 1040. Cuff 1300 may be flexible and made from a similar material to the wound retractor 1000 and shaped to fit therein, e.g., frusto-conically-shaped. In instances, cuff 1300 is made from a ridged or semi-rigid material to facilitate electrical cutting and to bias the tissue "T" as the tissue "T" is being externalized through the cuff 1300 (as detailed below).

Cuff 1300 also includes one or more spring-loaded ground guards 1200 that operably connect to the second lead 1015b to complete the circuit when engaged. More specifically, ground guards 1200 each include a lever arm 1204 pivotably mounted on the periphery of the wound retractor 1000 about a pivot 1203 at a proximal end thereof. The ground guards 1200 may be associated with either the cuff 1300 (as shown) or the wound retractor 1000 (not shown). Each lever arm 1204 is operably engaged to a spring 1207 that biases each lever arm 1204 towards the inner periphery of the cuff 1300. Alternatively, a torsion spring (not shown) may be utilized about the pivot 1203 to accomplish the same purpose.

A corresponding number of ground contacts 1205 are disposed on an inner periphery of the wound retractor 1000 toward a distal end thereof. Alternatively, a ground contact ring may be employed for this purpose. The distal end of each lever arm 1204 is disposed in concentric registration with the corresponding ground contact 1205 such that when each lever arm 1204 is forced outwardly (via the force of tissue "T" being pulled by a forceps or grasper 1500 through the distal end of the wound retractor 1000), each level arm 1204 contacts the corresponding ground contact 1205 and completes the electrical circuit. Once the electrical circuit is completed, energy is supplied to the cutting edge "C" to cut tissue "T" as it is being pulled through the wound retractor 1000 (and cuff 1300) and any excess tissue "Ti" is cut from the tissue specimen "T" as the tissue specimen "T" is pulled through the wound retractor 1000. The cut tissue "Ti" falls into the specimen bag 200 for later retrieval by the forceps 1500.

FIGS. 7A-7E show a cutting guard 2000 in accordance with the present disclosure that may be utilized with a wound retractor, e.g., wound retractor 100, and specimen bag 200. Cutting guard 2000 is configured to be placed and secured within the wound retractor 100 once positioned within incision "I" (See FIG. 1-3C). Various mechanical interfaces 2022 (FIG. 7A) may be utilized to secure the cutting guard 2000 to the wound retractor 100. A series of flares, ribs, snap-fit elements, and/or threaded elements may also be utilized to interface with or engage the proximal ring 120 or distal ring 140 of the wound retractor 100.

Cutting guard 2000 includes proximal and distal portions 2020 and 2040, respectively, having an elongated sheath 2030 therebetween that defines a lumen 2025 for externalizing tissue "T" therethrough. The lumen 2025 includes a flexible inner peripheral surface 2021 having electrically conductive ring contact 2125 disposed therein the purpose of which being explained in detail below.

Proximal portion 2020 is configured to securely engage the proximal ring 120 of wound retractor 100 and distal portion 2040 is configured to securely engage the distal ring 140 of wound retractor 100. Alternatively, cutting guard 2000 may be configured to engage incision "I" and couple to the specimen bag 200 (not shown) thereby eliminating the necessity of the wound retractor 100 depending upon a particular purpose. As discussed herein, the cutting guard 2000 will be described as working in conjunction with the wound retractor 100.

Cutting guard 2000 includes an elongated ground body 2112 having a proximal end 2120 and a distal end 2140. Ground body 2112 in configured for insertion into the lumen 2025 and includes a proximal opening 2150a and a distal opening 2150b for externalizing tissue "T" therethrough. The ground body 2112 is configured to receive the electrically conductive ring contact 2125 of flexible inner peripheral surface 2021 of cutting guard 2000 such that the electrically conductive ring contact 2125 and the ground body 2112 reside in concentric registration. A spring 2107 is configured to bias the electrically conductive ring contact 2125 and inner peripheral surface 2021 inwardly as depicted by arrows "A" in FIG. 7C. Electrical lead 2015b is operably and electrically connected to the ground body 2112 and to an electrical energy source (Not shown).

The distal end 2140 of cutting guard 2000 includes a cutting electrode 2142, e.g., ring electrode, that operably and electrically connects to electrical lead 2015a. Upon activation thereof, the cutting electrode 2142 cuts (or otherwise treats) tissue "T" in contact therewith. In other words, as tissue "T" is being externalized in the direction of arrow "C" through opening 2150b defined in the distal end 2140 of cutting guard 2000, excess tissue "Ti" that does not easily fit through opening 2150b forces the spring 2107 outwardly in the direction of arrow "B" causing the electrically conductive ring contact 2125 to touch the ground guard 2112 and complete the electrical circuit thereby activating the cutting electrode 2142. Alternatively, spring 2107 may act as the contact to complete the electrical circuit. The cutting electrode 2142 then excises excess tissue "Ti" that does not fit through opening 2150b which then falls into the specimen bag 200 for later removal (See FIG. 7E).

Spring 2107 acts as a safety that prevents activation of the cutting electrode 2142 except in oversized tissue "T" conditions. In other words, if tissue "T" is sized to fit through opening 2150b during externalization, the cutting electrode 2142 is not activated. Other safety mechanisms (not shown) may be employed to insure safe operation of the cutting guard 2000, e.g., safety switches, kill switches, etc. During any given procedure, the cutting electrode 2142 may be intermittently activated as needed when oversized tissue forces the electrically conductive ring contact 2125 to contact the ground guard 2112 during excess tissue conditions.

Electrically conductive ring contact 2125 may be replaced by a series of contacts (not shown) displayed in an array-like fashion around the inner periphery of ground guard 2112. Other types of known biasing mechanisms may also be employed to replace spring 2107, elastomeric rings, living hinges, compressible discs, etc.

Once a sufficient amount of the tissue specimen "T" is removed from the specimen bag 200 to facilitate removal of the specimen bag 200 through incision "I", any insufflation gases are withdrawn. The surgeon then removed the cutting guard 2000 and collapses and deforms the distal ring 140 of the wound retractor 100 using a forceps, grasper, or similar instrument and the distal ring 140 and specimen bag 200 are withdrawn through the incision "I". After the specimen bag 200 is removed, any tissue remaining therein can be removed from the specimen bag 200 for further examination or the specimen bag 200 can be discarded.

Figure 8:
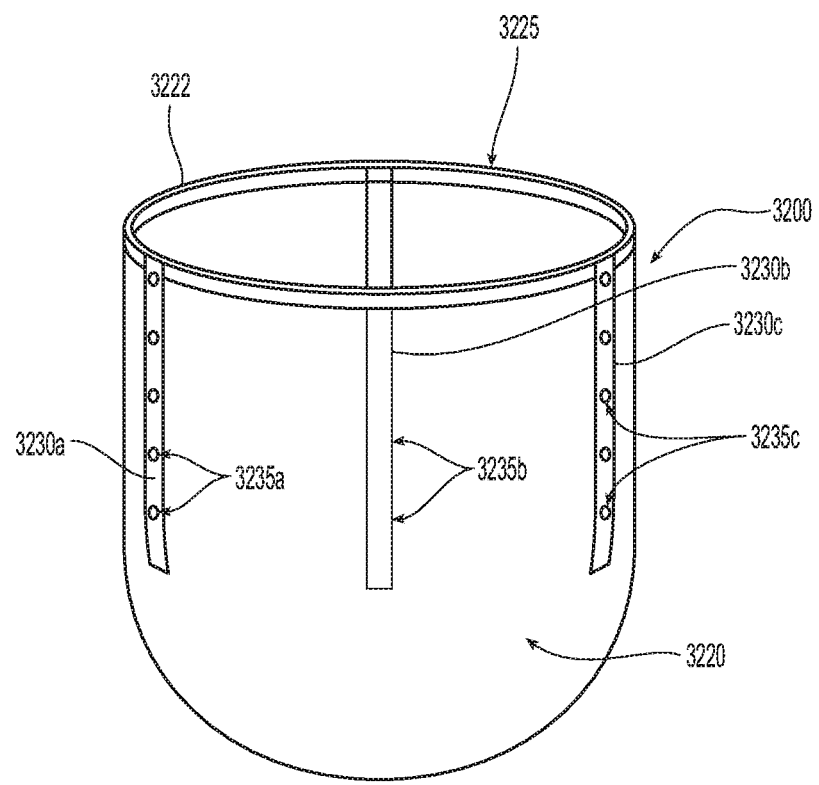
FIG. 8 is a schematic view a specimen bag in accordance with the another embodiment of the present disclosure.
Figure 9A:
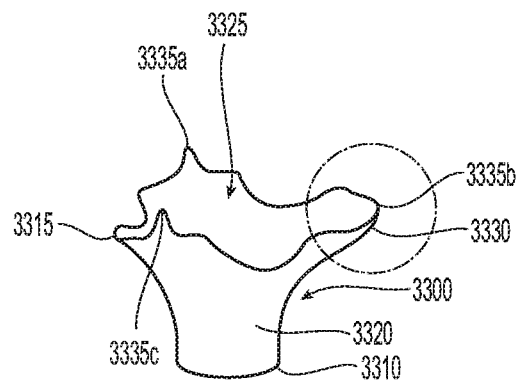
FIGS. 9A and 9B are schematic views of a cutting guard for use with the specimen bag of FIG. 8.
Figure 9B:
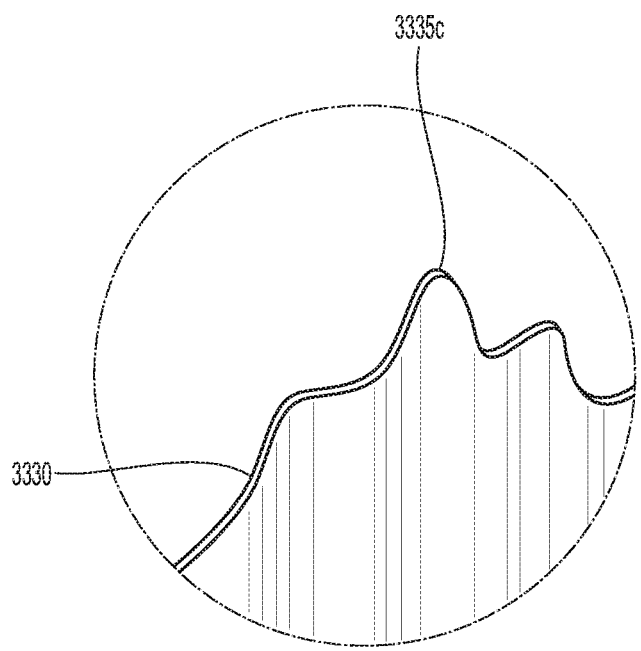

FIG. 8 shows another embodiment of a specimen container 3200 for use with a cutting guard 3300 to provide safe tissue extraction at the end of minimally invasive surgical procedures. Specimen container 3200 includes an outer or proximal rim 3222 that supports a specimen bag 3220 and that defines an inner cavity 3225 for containing a tissue specimen "T" therein. Specimen container 3200 also include a series of support ribs 3230a, 3230b and 3230c that extend into the inner cavity 3225 along the periphery of the specimen bag 3220. Each support rib, e.g., support rib 3230c, includes a series of mechanical interfaces, e.g., mechanical interfaces 3235a, 3235b, and 3235c operably engaged with support rib 3230c, that are configured to mechanically engage a corresponding interface (or plurality of interfaces) associated with cutting guard 3300, e.g., interfaces 3335c (See FIGS. 9A and 9B). The supporting ribs 3230a, 3230b and 3230c of the specimen container 3200 may be disposed about the perimeter of the specimen bag 3220 in an array-like manner.

The mechanical interfaces 3235a, 3235b, and 3235c of the specimen container 3200 may be notches, holes, ridges, tongue-and-groove, etc., which are designed to selectively engage the corresponding mechanical interfaces 3335a, 3335b, and 3335c (e.g., hooks, flanges, ramps, tongue-and-groove, fingers, key-like interfaces, etc.) of the cutting guard 3300. Each support rib 3230a, 3230b and 3230c may include any number of mechanical interfaces 3235a, 3235b, and 3235c that are configured to engage a corresponding number of mechanical interfaces 3335a, 3335b, and 3335c associated with cutting guard 3300. The mechanical interfaces associated with the cutting guard 3300 may be disposed on a proximal end 3315 of the body 3320, a distal end 3310 of the body 3320 or associated therebetween.

Figure 10A:
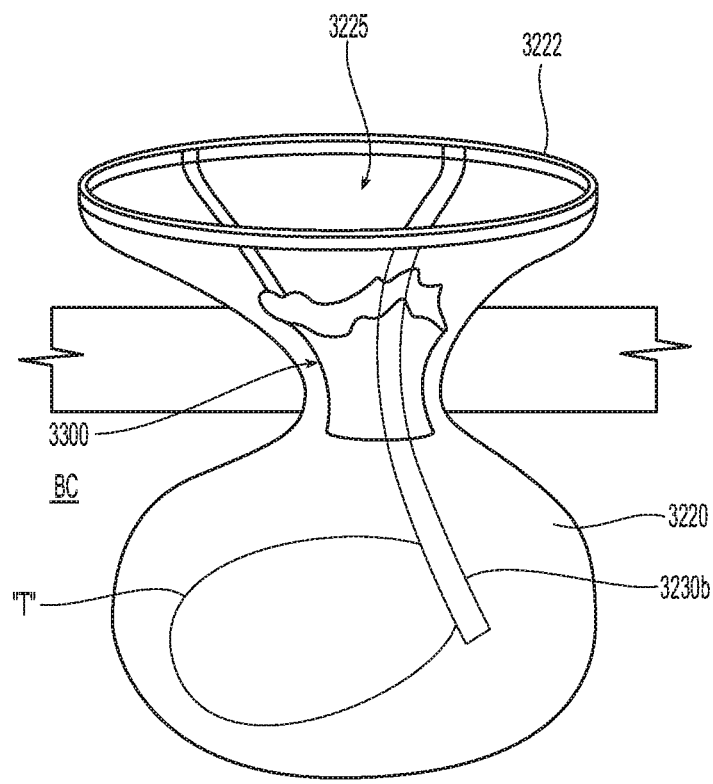
FIGS. 10A and 10B are schematic views of the specimen bag and cutting guard of FIGS. 8-9B shown in various stages of use.
Figure 10B:
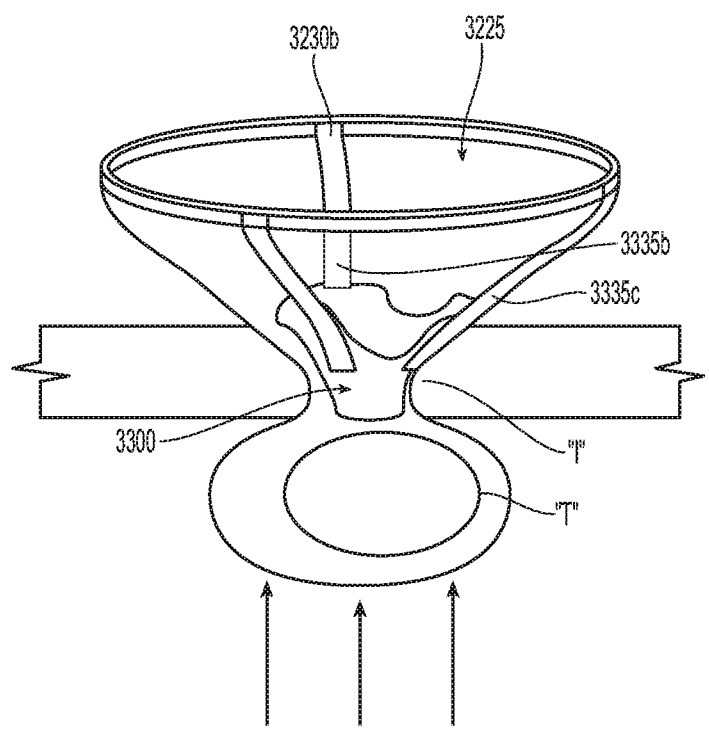

As best shown in FIGS. 10A and 10B after the specimen container 3200 is introduced into the body cavity "BC" through incision "I" and the tissue specimen "T" is loaded therein for extraction therefrom, the cutting guard 3300 is introduced into the neck of the specimen bag 3220 proximate the incision "I" and wedged therein towards the body cavity "BC". The mechanical interfaces 3235a, 3235b, and 3235c provide additional support to the specimen container to facilitate extraction. Moreover, the frustoconical shape of the cutting guard 3300 facilitates insertion of the distal end 3310 of the cutting guard 3200 into the incision "I" while leaving the proximal end 3315 outside of the incision. Further, the frustoconical shape of the container provides an active bias against the incision "I" (i.e., the incision provides a natural inward bias) when the cutting guard is disposed therein facilitating engagement of the corresponding mechanical interfaces, e.g., mechanical interface 3235c of rib 3230c and mechanical interface 3335c of cutting guard 3300. Moreover, the frustoconical shape allows the same cutting guard to be utilized with varying-sized incisions "I".

As the cutting guard 3300 is wedged toward the body cavity "BC", the plurality of mechanical interfaces 3335a, 3335b, and 3335c of the cutting guard 3300 align for engagement with the corresponding interfaces 3235a, 3235b, and 3235c of the specimen container 3200. The natural bias of the incision "I" coupled with any pressure associated with the body cavity "BC" facilitates engagement of the corresponding interfaces. The interactive locking of the cutting guard 3300 within the specimen bag 3220 also secures the specimen bag 3200 in place during externalization of the tissue specimen "T".

Once the cutting guard 3300 is secured within the specimen container 3200, one or more instruments (as described above) may be introduced into the specimen container 3200 to extract the tissue specimen "T" or excess portions thereof as needed. Moreover, the specimen bag 3220 or the specimen container 3200 may be furled around the proximal rim 3222 of the specimen container 3200 as needed to facilitate extraction and/or excision of the specimen "T". This allows a user to adjust the specimen container 3200 and the specimen bag 3220 as needed to proximate the tissue specimen "T" near the opening in the incision "I".

As can be appreciated, the combination of specimen container 3200 and the cutting guard 3300 eliminates the need for a wound retractor.

The wound retractor 1000, wound retractor 100, cutting guard 2000, cutting guard 3300 each for use in conjunction with the specimen bags 200, 3200 of the present disclosure provide safe tissue extraction at the end of minimally invasive surgical procedures. Diseased tissue may be removed from the body without seeding of spilled tissue cells inside the abdomen. The designs described herein allow for the surgeon to break up tissue without tearing the specimen bag 200, 3200 and possibly releasing tissue contents back into the body of the patient. The embodiments disclosed herein may also be used to remove any tissue or object from the body.

It will be understood that various modifications may be made to the embodiments disclosed herein. For example, various other methods for introducing specimen bags 200, 3200 of the present disclosure into the body of a patient may be used. Additionally, other specimen bag 200, 3200 shapes may be used. Further, the terminology of similar components with the various embodiments should not be construed as specific to any particular embodiment. Thus, the above description should not be construed as limiting, but merely as exemplifications of preferred embodiments. Those skilled in the art will envision other modifications within the scope and spirit of the claims appended hereto.

What is claimed is:

1. A kit for extracting a tissue specimen, comprising:
   a specimen container including:
   a proximal rim;
   a specimen bag operably supported about the proximal rim and depending therefrom, the proximal rim and the specimen bag defining an internal cavity therein; and
   a plurality of ribs depending from the proximal rim including a series of mechanical interfaces associated therewith and extending therealong;
   a cutting guard including:
   a body having proximal and distal ends and defining a shape therebetween, the distal end configured for insertion within the specimen container when disposed within an incision, the proximal end defining an opening therein configured to facilitate introduction of one or more surgical instruments therethrough; and
   at least one mechanical interface operably associated with the body of the cutting guard configured to selectively engage one of the series of mechanical interfaces of one of the plurality of ribs of the specimen container upon insertion of the cutting guard within the incision.

2. The kit for extracting a tissue specimen according to claim 1, wherein at least one of the mechanical interfaces of the cutting guard includes a projecting finger that is configured to engage one of the corresponding series of mechanical interfaces of one of the plurality of ribs of the specimen container as the cutting guard is inserted into the incision.

3. The kit for extracting a tissue specimen according to claim 1, wherein the shape of the cutting guard is frusto-conical to bias the at least one mechanical interface of the cutting guard into engagement with a corresponding one of the series of mechanical interfaces of one of the plurality of ribs of the specimen container when the cutting guard is inserted within the incision.

4. The kit for extracting a tissue specimen according to claim 1, wherein the at least one mechanical interface of the cutting guard includes a plurality of projecting fingers, each finger of the plurality of fingers configured to selectively engage a corresponding one of the series of the mechanical interfaces associated with each rib of the specimen container.

5. The kit for extracting a tissue specimen according to claim 1, wherein the plurality of ribs are disposed in an array-like fashion about an inner periphery of the specimen bag.

6. The kit for extracting a tissue specimen according to claim 5, wherein the at least one mechanical interface of the cutting guard includes a plurality of mechanical interfaces disposed in an array-like fashion about the proximal end thereof, the plurality of mechanical interfaces of the cutting guard disposed in registration with the plurality of ribs of the specimen container such that, upon insertion into the incision, each of the plurality of mechanical interfaces of the cutting guard selectively engages one of the corresponding series of mechanical interfaces of the plurality of ribs of the specimen container.

7. The kit for extracting a tissue specimen according to claim 1, wherein the at least one mechanical interface of the cutting guard includes a plurality of mechanical interfaces disposed in an array-like fashion about the proximal end thereof.

8. The kit for extracting a tissue specimen according to claim 1, wherein the specimen bag is configured to be furled about the proximal rim to facilitate externalization of a tissue specimen.

* * * * *